United States Patent
Hieronimi

(10) Patent No.: US 8,938,208 B2
(45) Date of Patent: Jan. 20, 2015

(54) SYSTEM FOR DETECTING HIGH-FREQUENCY TRANSCEIVERS AND USES THEREOF

(76) Inventor: Christian Hieronimi, Schwabmunchen (DE)

( * ) Notice: Subject to any disclaimer, the term of this patent is extended or adjusted under 35 U.S.C. 154(b) by 23 days.

(21) Appl. No.: 13/818,232

(22) PCT Filed: Aug. 12, 2011

(86) PCT No.: PCT/EP2011/063962
§ 371 (c)(1),
(2), (4) Date: Feb. 21, 2013

(87) PCT Pub. No.: WO2012/025411
PCT Pub. Date: Mar. 1, 2012

(65) Prior Publication Data
US 2013/0184005 A1     Jul. 18, 2013

(30) Foreign Application Priority Data
Aug. 27, 2010  (DE) .......................... 10 2010 037 195

(51) Int. Cl.
| | | |
|---|---|---|
| H04M 11/00 | (2006.01) | |
| H04W 64/00 | (2009.01) | |
| G01S 5/02 | (2010.01) | |
| G01S 13/76 | (2006.01) | |
| G01S 13/87 | (2006.01) | |
| A61N 5/10 | (2006.01) | |

(52) U.S. Cl.
CPC ............ *H04W 64/00* (2013.01); *H04W 64/003* (2013.01); *G01S 5/0247* (2013.01); *G01S 5/0252* (2013.01); *G01S 5/0289* (2013.01); *G01S 13/76* (2013.01); *G01S 13/874* (2013.01); *A61N 5/1049* (2013.01); *A61N 2005/1051* (2013.01)
USPC ...................... 455/403; 455/414.1; 455/456.1

(58) Field of Classification Search
CPC . H04W 64/003; H04W 64/006; H04W 64/00; H04W 72/08; H04W 76/04
USPC ............. 455/403, 404.2, 456.1, 456.2, 456.6, 455/11.1, 13.1
See application file for complete search history.

U.S. PATENT DOCUMENTS

| | | | |
|---|---|---|---|
| 6,710,719 | B1 | 3/2004 | Jones et al. |
| 8,111,154 | B1* | 2/2012 | Puri et al. .................. 340/539.13 |
| 2003/0028323 | A1* | 2/2003 | Zeitler et al. ................... 701/219 |
| 2005/0255864 | A1* | 11/2005 | Kent et al. ................... 455/456.5 |
| 2006/0267833 | A1 | 11/2006 | Langford et al. |
| 2008/0191846 | A1* | 8/2008 | Chang ......................... 340/10.41 |
| 2009/0281419 | A1 | 11/2009 | Troesken et al. |
| 2010/0134257 | A1* | 6/2010 | Puleston et al. .............. 340/10.4 |
| 2010/0217723 | A1* | 8/2010 | Sauerwein et al. ........... 705/337 |
| 2010/0321246 | A1 | 12/2010 | Troesken et al. |
| 2011/0316748 | A1* | 12/2011 | Meyer et al. ................... 342/451 |
| 2012/0092134 | A1* | 4/2012 | Stern et al. .................... 340/10.1 |

(56) References Cited

FOREIGN PATENT DOCUMENTS

| | | |
|---|---|---|
| DE | 10 2005 011 126 A1 | 9/2006 |
| DE | 10 2006 029 122 A1 | 12/2007 |
| DE | 10 2008 013 611 A1 | 9/2009 |
| DE | 10 2008 035 633 A1 | 12/2009 |
| DE | 10 2008 053 176 A1 | 4/2010 |
| GB | 2 332 052 A | 6/1999 |

OTHER PUBLICATIONS

International Search Report mailed Jan. 23, 2012, issued in corresponding International Application No. PCT/EP2011/063962, filed Aug. 12, 2011, 2 pages.

International Preliminary Report on Patentability mailed Mar. 5, 2013, issued in corresponding International Application No. PCT/EP2011/063962, filed Aug. 12, 2011, 11 pages.

German Patent and Trademark Office Search Report mailed Jul. 19, 2011, issued in corresponding German Application No. DE 10 2010 037 195.5, filed Aug. 27, 2010, 5 pages.

Itzigehl, M., et al., "Visualisierung als Werkzeug für effiziente Interpretationen RFID-generierter Daten und Sensor Informationen," 2008, <http://www.amirsemmo.de/attachements/045_snio_article_2008.pdf>, 13 pages (includes English abstract).

\* cited by examiner

Primary Examiner — Jean Gelin
(74) Attorney, Agent, or Firm — Christensen O'Connor Johnson Kindness PLLC

(57) ABSTRACT

The invention relates to high-frequency technology. In particular, the present invention relates to a system for detecting the position and/or location of at least one high-frequency transceiver with at least one receiving antenna set up such that high-frequency signals transmitted by the at least one high-frequency transceiver can be received by means of said receiving antenna, at least one transmitting antenna set up for transmitting high-frequency signals of at least one frequency band being intended to be received by the at least one high-frequency transceiver and thereby in turn causing the transmitting of high-frequency signals by the at least one high-frequency transceiver, at least one first antenna signal processing device connected to the at least one receiving antenna being set up for analyzing the high-frequency signals received by the at least one receiving antenna in order to therefrom derive a spatial position and/or location and an identification of the transmitting high-frequency transceiver, and at least one data processing device being at least indirectly connected to the first antenna signal processing device and receiving information therefrom about the position, location, and/or identification of the transmitting high-frequency transceiver, where a data structure is provided in a first memory device connected to the at least one data processing device and at least partially comprising a virtual representation of the space supplied by the antenna field of the at least one transmitting antenna, where the virtual representation comprises information about the target position and/or location of at least one high-frequency transceiver having a predefined identification, and transformation information is available to the at least one data processing device on the basis of which an actual position and/or location of at least one high-frequency transceiver having a predefined identification within the virtual representation is associated on the basis of the position, location, and/or identification information obtained from the first antenna signal processing device, and the at least one data processing device carries out a comparison between the target position and the actual position and/or location of a high-frequency transceiver of a predefined identification within the virtual representation, outputting a signal representing a "match" or "no match" as the result of the comparison for further processing.

20 Claims, 5 Drawing Sheets

SYSTEM FOR DETECTING HIGH-FREQUENCY TRANSCEIVERS AND USES THEREOF

The present invention relates to high-frequency technology. In particular, the invention relates to a system for detecting the position and/or location of at least one high-frequency transceiver and applications of this system.

High-frequency transceivers are known in prior art inter alia in the form of RFID-markers or RFID-tags (Radio Frequency Identification Tag). These kinds of markers or tags are already found in numerous applications, both in manufacturing, for example, for tracing and/or controlling production processes, as well as in consumer goods retailing, for example, for tracking the flow of goods, for authenticity verification and the like.

Furthermore, DE 10 2007 062 843 A1 shows a system with which the electromagnetic signals emitted by the RFID-tags are by means of suitable reception systems with directional properties used to locate the tags and track their movement, respectively. DE 10 2006 029 122 A1 describes locating a medical instrument based on an RFID-tag attached thereto.

It has shown for these known systems that they provide little or no other relevant information beyond simple localization of the RFID-tag or tags, respectively.

It is therefore an object of the invention to provide a system for detecting high-frequency transceivers (such as RFID-tags) which improve known systems at least partially, and in particular at least partially enable automated evaluation of the detected position or location information.

These and other objects are satisfied by a system for detecting the position and/or location of at least one high-frequency transceiver having the features of claim 1. Preferred uses of the system according to the invention are the subject matter of claim 20. Preferred embodiments are the subject matter of the respective dependent claims.

According thereto, a system for detecting the position and/or location of at least one high-frequency transceiver according to the invention comprises at least one receiving antenna set up such that high-frequency signals transmitted by the at least one high-frequency transceiver can be received by means of said receiving antenna, and at least one transmitting antenna set up for transmitting high-frequency signals of at least one frequency band provided for being received by the at least one high-frequency transceiver and thereby in turn causing the transmitting of high-frequency signals by the at least one high-frequency transceiver, at least one first antenna signal processing device connected to the at least one receiving antenna being set up for analyzing the high-frequency signals received by the at least one receiving antenna in order to derive a spatial position and/or location and an identification of the transmitting high-frequency transceiver. At least one data processing device is at least indirectly connected to the first antenna signal processing device and receives information therefrom about the position, location, and/or identification of the transmitting high-frequency transceiver.

According to the invention, a data structure is provided in a first memory device connected to the at least one data processing device, at least partially comprising a virtual representation of the space supplied by the antenna field of the at least one transmitting antenna, wherein the virtual representation comprises information about the target position and/or location of at least one high-frequency transceiver having a predefined identification, Transformation information is available to the at least one data processing device on the basis of which an actual position and/or location of at least one high-frequency transceiver having a predefined identification within the virtual representation is associated on the basis of the position, location, and/or identification information obtained from the first antenna signal processing device, and the at least one data processing device carries out a comparison between the target position and the actual position and/or location of a high-frequency transceiver of a predefined identification within the virtual representation, outputting a signal representing "match" or "no match" as the result of the comparison for further processing.

A system according to the invention designed like this has the advantage that it can not only detect merely the spatial position and/or location of a high-frequency transceiver or its antenna, respectively, in relation to the receiving antenna, but it also provides in particular the possibility to absolutely determine the position and/or location of at least one high-frequency transceiver (actual position or location, respectively) in a virtual representation of the space (virtual space) supplied by the transmitting antenna field and to set it in relation to a position and/or location stored with the virtual representation (target position or location, respectively).

In this, the target position and/or location within the virtual representation was preferably either determined by one or more such positions and/or locations being directly defined in the virtual representation, or by measuring at least one target object having respective high-frequency transceivers attached to it at predefined locations and/or in predefined patterns, and the recording of the positions and/or locations of the high-frequency transceivers thus determined and their registration as target positions and/or locations in the virtual representation.

In this, a special feature of the present invention is, that by means of the transformation information being available to the at least one data processing device, transformation of the position, location and/or identification information of the high-frequency transceiver obtained from the at least one first antenna signal processing device can be transformed into the virtual representation (and preferably also out of it) and that there is therefore a unique relationship between the virtual representation and that from the antenna field of the at least one transmitting antenna, preferably a biunique relationship.

The virtual representation therefore preferably represents a virtual illustration of at least a portion of the space supplied by the transmitting antenna and/or detected by the receiving antenna into which all the measured position, location and/or identification information is transposed and in which further processing of the data obtained can be performed in a simple manner.

The transformation information is in one embodiment of the invention preferably obtained by measurement (calibration)—repeated as required—of the transmitting antenna field by a reference object and made available to the at least one data processing device by permanent storage of the same in a memory device at least indirectly connected to the data processing device, such as a flash ROM, a hard disk drive and/or the like. Such a determination of transformation information is particularly advantageous because, in this manner, the field distortions of both the electromagnetic fields emitted by the transmitting antenna as well as the field distortion of the electromagnetic fields emitted by the high-frequency transceivers due to components, interfering objects and/or sources of interference disposed within the (real) space, i.e. in the transmitting antenna field can be accounted for in the transformation, thereby ensuring the correct and possibly corrected actual position and/or location of the high-frequency transceiver in the virtual representation (i.e. the virtual space).

By means of the transformation information, there is quasi an exact mapping of the real space to the virtual space, but preferably in the domain of the transmission field or the fields respectively transmitted by the high-frequency transceivers. Suitable transformation information is, for example, in the form of a complex matrix, with which possibly a symbolic transformation of the detected position and/or location information could be performed, or a possibly multidimensional numerical number field, which can then be used for numerical transformation—if necessary comprising inter- or extrapolations.

In a further embodiment, which is applicable separately and/or additionally, there is an option to determine and/or to calibrate transformation information and possibly also verify it in the determination of the actual position and/or location of at least one stationary high-frequency transceiver with pre-defined identification when relating it to the target position and/or location in the virtual representation, where in the virtual representation, the position of this high-frequency transceiver is preferably already defined during production or installation of the system and possibly marked as being unchangeable.

In this manner, continuous recalibration is possible or at least permanent control that the initial or a subsequent calibration is still reliably correct, because any deviation of the measured actual position and/or location of the fixed target position and/or location can result in a corresponding error message. For example, a change of components, interfering objects and/or sources of interference disposed within the real space, i.e., i.e. in the transmitting antenna field can thus also be detected and it can thus be prevented that measuring errors resulting therefrom and their mapping in the virtual representation occur.

In still another embodiment, which is applicable separately and/or additionally, there is an option to determine and/or to calibrate transformation information and possibly also verify it in the selective and/or continuous measurement of the directional characteristic of the at least one receiving antenna and/or the at least one transmitting antenna and to relate these determined characteristics to the virtual representation. This is in particular possible and advantageous when a plurality of high-frequency transceivers is measured, i.e. their position and/or location is determined and a change of the directional reception characteristic is detected due to the differences in the measurement results of transceivers being respectively adjacent or otherwise in relation, e.g. the field strengths transmitted and/or received by the high-frequency transceivers. The latter could, for example, by means of measurement and return transmission of the measured reception field strength from the transceiver/s be transmitted back via the receiving antenna to the system.

In this manner, continuous recalibration is also possible or at least permanent control that the initial or a subsequent calibration is still reliably correct, because any deviation of the measured directional characteristic of the at least one receiving antenna and/or the at least one transmitting antenna can result in an error message. Like this as well, a change of components, interfering objects and/or sources of interference disposed within the real space, i.e. in the transmitting antenna field can thus also be detected and it can thus be prevented that measuring errors resulting therefrom and their mapping in the virtual representations occur.

The possibilities described above or below of determining or verifying the calibration of the transformation information can also serve selective detection of the arrangement of certain components and/or the presence of individuals, and thus detection of certain application situations In such a case, no recalibration of the transformation information is therefore required but possibly only access by the data processing device to further transformation information which was respectively prepared or created for the specific application situation.

For example, in this manner, for a space in which a metallic object is arranged movably in a circle, which during its movement along the circular path influences and/or distorts the electromagnetic field or fields which are transmitted by the transmitting antenna or antennas and/or by the high-frequency transceiver or transceivers differently depending on the location, for different locations of the object, further transformation information and/or one or a plurality of error matrices correcting the transformation information can be generated, which are then each used in the allocation of then measured position and/or location information to the actual positions and/or locations in the virtual representation, in order to thus ensure reliable and accurate transformation of the measured position and/or location information into the virtual space (and possibly also out of it) even with the object having different positions.

In a preferred embodiment of the invention, the at least one receiving antenna is composed of a matrix of several inter-acting receiving antennas, where the coaction is controlled preferably by a second antenna signal processing device and/or the first antenna signal processing device. Such a coaction of several receiving antennas in the form of a matrix warrants improved directional characteristics of the receiving antenna as well as secure detection of all high-frequency transceivers disposed in real space, even if their transmission signals are dampened by strongly dampening elements, such as metal objects or body parts.

It is also particularly advantageous with such a matrix-like arrangement of receiving antennas, if the transformation information comprises individual transformation information as subcomponents for each of the transmitting and/or receiving antennas coacting in the matrix. In this manner, transformation of the actual position and/or location in the virtual representation can be performed by at least one data processing device by means of a transmission signal of a high-frequency transceiver recorded by a plurality of receiving antennas using the transformation information respectively valid for this transmission/reception system and any deviation of the positions within the virtual representation determined by the individual transmission/reception systems can output an error message, by means of which the need for re-calibration can be displayed.

Such an embodiment therefore does not only provide a system wherein the plurality of reception systems of the matrix of receiving antennas is calibrated to each other (by corresponding individual transformation information and the associated virtual space), but an inherent verification possibility for the correctness of the individual transformation information is given, so that changes of the components, interfering objects, and/or sources of interference disposed in the real space, i.e. the transmitting antenna are again detected and it can thereby be prevented that measurement errors and their representation in the virtual representation occur.

In a particularly preferred embodiment, the at least one data processing device is mobile, and in particular a portable data processing device, preferably a portable computer (laptop), a tablet computer, a smart device or the like. This allows easy work with the system according to the invention, in particular in applications in which repositioning of a high-frequency transceiver occurs or can occur before the data processing device outputs the result of the comparison between the actual position and/or location and the target position and/or location as being a "match".

In a particularly preferred embodiment of the present invention, the first data processing device comprises a plurality of interacting data processing devices, where data communication between the plurality of data processing devices is effected preferably by means of optical, radio or wireless data connections. In this, in particular interaction of a stationary data processing device with a mobile data processing device can be advantageous, especially when in the framework of the data processing, large volumes of data are to be processed or to be stored, and therefore due to the limited capacity of a portable data processing device in terms of computing power and/or storage capacity, performance loss in processing is to be feared. The mobile data processing device could in this case be at least partially a kind of one input-output unit for the stationary data processing device.

Moreover, cooperative interaction of several data processing devices, between which data communication occurs, can of course be used also for applications in which determination of the actual position and/or location according to the invention occurs at places being entirely different from that of the output of the comparison, wherein to this end, the distance of the places is irrelevant, since after the transformation of the measured positions and/or locations of the transceivers in the real space into the virtual space, any further processing can only take place in the virtual space, where this processing may be performed anywhere on the basis of known data transmission methods and means For example, such a feedback could occur for re-positioning of individuals or objects or for controlling a remote-controlled movement, where due to the virtual representation and the transformation information, any deviation from the predefined position and/or the movement path can be reliably prevented.

In a particularly preferred embodiment of the present invention, the at least one receiving antenna, the at least one transmitting antenna and/or the first and/or second antenna signal processing device are set up such that they can receive and transmit, respectively, on a plurality of frequency bands. Preferably, the at least one receiving antenna, the at least one transmitting antenna and/or the first and/or second antenna signal processing device forming transmission and reception systems in different combinations are set up such that transmitting or receiving high-frequency signals is possible at least substantially simultaneously or variably in the frequency domain across a plurality of frequency bands.

It is possible by means of such a configuration to improve determination of the position and/or location of at least one high-frequency transceiver possibly in a multi-stage process until the desired accuracy of the defined position and/or location has been reached. For this, for example, determination of the position and/or location of the at least one high-frequency transceiver occurs at a low transmission and/or reception frequency, i.e. a longer wave-length, and thereafter, for improving the measurement, at least one determination of the position and/or location of the same high-frequency transceiver at a higher transmission and/or reception frequency, i.e. a shorter wavelength.

The transmission and/or reception frequency is here to be understood as being both the transmission frequency of the at least one transmitting antenna as well as that of the at least one high-frequency transceiver, where the reception frequency likewise can be both the reception frequency of the at least one receiving antenna, as well as that of the at least one high-frequency transceiver.

Another possibility is provided by the continuous change of the transmission and/or reception frequency during the measurement, so that by means the resulting (and measurable) phases and amplitudes in the region of at least one receiving antenna being highly distance- and angle-dependent, very exact determination of the position and/or location of at least one high-frequency transceiver is possible. For example, already a so-called sweep of the transmission signal of the high-frequency transceiver or transceivers across a relatively small frequency range would during the measurement be able to lead to very precise determination of the position and/or location of the high-frequency transceiver.

The at least one transmission and/or reception devices are in the system according to the invention preferably designed such that—not necessarily simultaneous—transmission and/or reception of frequencies in the high kHz-range, and optionally and preferably also in the low, middle and/or high MHz-range, further preferably in the low, middle and/or high GHz-range, and beyond that also up into THz-range is enabled, up to wavelengths in the far infrared. Such frequency ranges can be generated and emitted or received, respectively, in different ways which are known in prior art.

It is preferable, however, that in cases of multiply employed transmission and/or reception devices, i.e. combinations of transmitting and/or receiving antennas with their respectively associated antenna drivers and antenna signal processing devices, they can be designed for respectively different transmission and/or reception frequency ranges, so that, for example, a transmitting antenna (together with associated components and receiver devices) supplying the entire real space is operated in the MHz-range, whereas an antenna matrix simultaneously supplying only a relatively small sub-region of the space is operated in GHz-range. Due to the different frequency ranges with which the respective transmission and/or reception devices are operated and the various influences of objects, interference components, etc. associated therewith in the space, in such a case, the first and/or each further data processing device preferably also has different transformation information (and possibly error matrixes) available for the transmission and/or reception frequencies and fields respectively used in order to be able to reliably and correctly transform the position and/or location detected by each of the transmission and/or reception devices for each system comprising the transmission and/or reception device including associated components which are employed for processing the position and/or location information into the virtual space (and possibly out of it).

Such an embodiment also enables examining the actual positions and/or locations detected by different transmission and/or reception devices or systems in terms of whether they match, and therefore not only provides the possibility of redundant position and/or location determination but also enables—as needed—a validation of the measurements of different systems and thus a plausibility check, which is of advantage in particular for applications with high accuracy requirements.

Frequency mixing is merely mentioned as an illustration by way of example as a possibility for producing transmission and/or reception frequencies—also dynamically changing—across certain frequency ranges. It is essential that the accuracy of the position and/or location determination increases already with the use of higher transmission and/or reception frequencies solely due to the shorter wavelength and both the higher measurement accuracy associated therewith as well as the possibility of using more compact antennas, for which reason sometimes—depending on the required accuracy of the position and/or location determination—the use of very high frequencies can be appropriate.

In a particularly preferred embodiment of the invention, the at least one receiving antenna and/or the first and/or second antenna signal processing device is stationarily connected to the mobile data processing device and preferably fixedly attached thereto. For example, the windings of flat antennas are mounted as a receiving antennas on the rear side of the screen or of the housing, respectively, of a portable computer so that measurement of the positions and/or locations of the preferably plurality of high-frequency transceivers is performed from the perspective of the mobile data processing device.

In order to in this case obtain clear and preferably biunique information of the actual position and/or location of the at least one high-frequency transceiver between the virtual representation and the real space, the location and/or position of the mobile data processing device is preferably to be determined on the basis of the transformation information also accessible by it regarding the virtual representation and/or at least one actual position and/or location to be determined of at least one high-frequency transceiver. For this, it is preferable to use at least one stationary high-frequency transceiver with predetermined identification, the position and/or location of which by the transmission/reception system (i.e., a combination of a transmitting and/or a receiving antenna and the antenna signal processing device), which is connected to the mobile data processing device and is to this end determined, and subsequently relating this detected position and/or location to the target position and/or location of the corresponding transceiver within the virtual representation, where in the virtual representation, the position of this high-frequency transceiver is preferably defined during production or set-up of the system and possibly marked as unchangeable.

By means of this relating, a kind of determination of additional transformation information therefore occurs, making it possible to uniquely map the positions and/or locations of the high-frequency transceivers determined by the mobile data processing device to the virtual representation, or to transfer their target position and/or location from the perspective of the mobile data processing device into the real space. The comparison between the actual position and/or location and the target position and/or location can then also occur "from the perspective" of the mobile data processing device, which can be of significant importance in particular for the output of the result.

In connection with this embodiment of the invention, but also independently of the attachment of the transmitting and/or receiving antennas and/or the antenna signal processing device on the mobile data processing device, it may be of advantage to provide the mobile data processing device with one or more high-frequency transceivers, by means of which exact determination of the position and/or location of the mobile data processing device with respect to or within the virtual representation is likewise enabled by measuring the respective high-frequency transceiver.

Both in this manner as well as in the one described above, the orientation of the mobile data processing device can be determined within the virtual representation and thereby, possibly by using the transformation information, regarding the real space. Matching of the reference system of the mobile data processing device to that of the virtual representation quasi takes place based on having additional transformation information being determined creating a unique and preferably a biunique relationship between the virtual space or the virtual representation, respectively, the real space from the "perspective" of the mobile data processing device, and possibly from the "perspective" of the transmission and/or reception system. In particular for the output functions described further below of the system according to the invention in connection with a mobile data processing device, this may be particularly advantageous.

In one embodiment of the invention, the at least one transmitting antenna is simultaneously also the at least one receiving antenna. Although this may seem generally advantageous, it is also possibly of advantage to have a separation of the transmission and reception system in terns of location. Especially in cases where the receiving antennas and associated components are disposed on a mobile data processing device, for example, energetic aspects could be in favor of designing the transmission system as being independent of the receiving antenna.

A transmission system not being attached to the mobile data processing device, but, for example, to the ceiling of a room and thereby being supplied via stationary power sources and possibly via a stationary data processing device can, for example, emit the signals necessary for activating, controlling, programming and/or querying the high-frequency transceivers, where, the signals emitted by the high-frequency transceiver o transceivers can thereafter be received and processed by the reception device as it is attached to the mobile data processing device. By means of such separation, the energetic resources of the mobile data processing device can be preserved while simultaneously obtaining relatively high field strengths, to the extent that this is required.

In a preferred embodiment of the present invention, the at least one data processing device, or a data processing device connected to it, comprises a display device outputting a graphic representation of the actual position and/or location of the at least one high-frequency transceiver, the target position and/or location of the at least one high-frequency transceiver and/or the virtual representation.

Preferably, the display device is mounted well visible for a user, such as on a wall of a room, and/or displaying is effected by a display device of the mobile data processing device. Alternatively or additionally thereto, it can be provided to have the display be effected by video or laser projection, wherein for example, the target and actual positions and/or locations of the high-frequency transceivers is indicated by selective illumination of an object or of a human. Further alternatively or additionally to the previous display devices, a user-portable display device can be provided which is mounted, for example, in the form of a pair of spectacles performing an image projection of the display onto the retina of the user.

The graphical output of the actual and/or target position and/or location, as well as possibly of the virtual representation allows, for example, a present user of the system to recognize to what extent and in what manner repositioning and/or rearrangement of the high-frequency transceiver must be made in order for the data processing device, as a result of the comparison between the actual position and/or location and the target position and/or location of this high-frequency transceiver, to output a "match".

In a preferred embodiment of the present invention, in the event that the data processing device as a result of the comparison of the target to the actual position and/or location of the at least one high-frequency transceiver outputs a signal for further processing representing "no match", a displacement vector is formed in the virtual representation between the actual position and/or location and the target position and/or location of the at least one high-frequency transceiver, and preferably displayed together with the virtual representation by means of the display device. In this way, it is particularly easy for a user of the system to detect by which kind of rearrangement or displacement all actual positions and/or locations can be matched with the respective target positions, and/or a locations of preferably a plurality of high-frequency transceivers possibly within the accuracy required for the positioning. After or during displacement or rearrangement, the position and/or location of the high-frequency transceivers, and possibly the representation for the user is then adapted in order to receive an appropriate response to the performed displacement or rearrangement.

More preferably, the possibly continuously determined displacement vector additionally serves as the basis for controlling at least one actuator element in order to automatically and without any manual intervention by the user bring the at least one high-frequency transceiver into its target position and/or location. This can occur possibly subject to the required positioning accuracy of individual high-frequency transceivers, in particular when using several high-frequency transceivers in cases with a variety of degrees of freedom. In this manner, it is possible by the system according to the invention to obtain not only a control function for repositioning and/or storage of at least one high-frequency transceiver, but beyond that, automatic adjustment or correction, respectively, of the positioning and/or storage of at least one high-frequency transceiver.

In this way it is also possible, in the event that one and the same application situation, to sequentially "run through" a plurality of target positions and/or locations of at least one high-frequency transceiver in that every time when the data processing device outputs a "match" between the target and the actual position and/or location for the at least one high-frequency transceiver, a new (or the next) target position and/or location for this transceiver is positioned in the virtual representation and, based thereupon, a displacement vector is determined. This displacement vector can then serve as a basis for controlling automatic displacement of the at least one high-frequency transceiver by at least one actuator element. In this manner, sometimes very complex trajectories of a high-frequency transceiver can be "run", which of course means that the objects on which the respective high-frequency transceiver or transceivers are disposed are guided substantially along the same trajectory.

In a further preferred embodiment of the present invention, graphical output of the comparison result occurs on the display device or devices, for example in the form that the comparison result is at least partially output in the form of a color-coded image output such as a green field or a red field, by outputting text result messages, such as "OK" or "FAIL", respectively, when the data processing device outputs a signal representing a "match" or "no match" as the comparison result. Particularly preferably, such simple and quick visually detectable information regarding the match of the target with the actual positions and/or locations of individual or all high-frequency transceivers can be integrated into the graphic display, in that, for example, the target and actual positions and/or locations of the high-frequency transceivers are displayed as dots within the graphically rendered virtual representation, where the dot for a "match" is marked in green and for "no match" in red. This shows the user in a visually detectable quick and reliable manner, when the actual position and/or location of the at least one high-frequency transceiver differs from the target position and/or location.

In addition to or instead of graphical output of the comparison result, voice output can also occur and preferably a release or a lock of at least an interlock, preferably at least a software interlock, by which other processes can possibly be triggered and/or controlled. For example, a system according to the invention can be set up such that only after a match of the target with the actual positions and/or locations of certain predetermined or all high-frequency transceivers, a relay is actuated switching on the power supply for other systems or devices. In this way it can be ensured for a variety of applications, that without proper positioning and/or repositioning of some or all high-frequency transceivers, no further processes are executed which due to incorrect positioning could possibly bear consequences in causing damage and/or being dangerous. Such applications are discussed by way of example further below in the context of the detailed description.

In addition, by means of the identification information that can be associated with the high-frequency transceivers, it can be also be ensured that there is no confusion of different transceivers, thereby incorrectly displaying a "match" or even a release of an interlock.

In one embodiment of the invention, the virtual representation comprises information on the required accuracy of the position and/or location match of the at least one high-frequency transceiver, where, in particular, respective information on the required accuracy of the position and/or location match between the target and the actual position and/or location of a high-frequency transceiver is delivered in combination with the target position and/or location of the at least one high-frequency transceiver with the respectively predefined identification, preferably within the virtual representation. Alternatively, the information on the required accuracy of the position and/or location match between the target and the actual position and/or location of a high-frequency transceiver can also be stored independently of the virtual representation, where unique allocation of the "match" of the position and/or location match to the respective transceivers of the virtual representation can preferably be created to the respective unique identification of the high-frequency transceiver.

Preferably, the data processing device, as a result of the comparison of the target to the actual position and/or location of the at least one high-frequency transceiver, outputs a signal representing a "match" or "no match" for further processing, if the actual position and/or location of at least one high-frequency transceiver matches its target position and/or location in the virtual representation within the required accuracy specified. In this manner, the signals representing a "match" or "no match" are then in the embodiments of the invention processed as described above but also as described further below, in particular, graphic output of such a match can occur, a release of interlocks and the like, if a "match" is detected within the "accuracy" defined for one or more transceivers by the system.

In this manner it is possible, that a kind of different weighting of the accuracies of the position and/or location match of different high-frequency transceiver is performed such that, for example, from a plurality of transceivers, the match of the target to the actual position and/or location of a transceiver must be particularly precise, whereas for other transceivers, a position and/or location match being less accurate is sufficient. Thereby, "accuracies" of the entire arrangement of high frequency transceivers are possible tailored to the respective application of the system according to the invention.

In a particularly preferred embodiment of the present invention, the at least one data processing device and/or a further data processing device is connected thereto having at least one external image recording device, where the external image recording device can be arranged for example in the region of the transmitting and/or receiving antennas or also in a position favorable for imaging recording. For the case of application of a mobile data processing device as a first or a further data processing device, preferably, the mobile data processing device preferably comprises an integrated image recording device. Preferably, the image recording device is a video camera, particularly preferably a high-resolution video camera or the like.

In a particularly preferred embodiment, the image recording device is, during recording and/or processing of the virtual representation and/or the application of the system, used to record images, for example, for guidance and/or control purposes. It is preferably also provided, that images recorded by the image recording device are displayed on the display device or devices of the first and/or further data processing devices.

More preferably, at least one image recorded by the external and/or integrated image recording device is stored in the memory device together with or in connection to the virtual representation, preferably during creation of the latter. In connection with displaying the virtual representation, the recorded image can then be displayed on at least one display device, so that a possible deviation of the arrangement of components, individuals and/or other objects can be easily perceived visually and be corrected.

Preferably, the at least one image recorded by the image recording device is subjected to image processing prior to being stored, in particular to contrast enhancement, segmentation, edge detection, subtraction and the like, where possibly contours in the recording situation existing during creation of the virtual representation can be enhanced, thereby achieving improvement of the visual perception during rendition.

Particularly preferably, the image recorded and/or stored by the recording device is displayed together with the actual position and/or location, the target position and/or location, and/or the virtual representation. This can be done for example by displaying a kind of so-called "augmented reality", in which a video image recorded live by the image recording device is superimposed with graphical elements indicating the target and/or actual positions and/or locations of the high-frequency transceivers and/or the virtual representation.

In this embodiment of the present invention, performance of the system according to the invention comes into its own, especially when the at least one first data processing device is a mobile data processing device comprising an integrated image recording device. By detecting the position and/or location of the mobile data processing device, its camera angle can be determined in relation to the virtual representation and the respectively stored target position and/or location of the at least one high-frequency transceiver and be superimposed to video images recorded by the image recording device in the correct position and perspective. Likewise, the actual position and/or location of the at least one high-frequency transceiver measured by the system can be detected and superimposed in the correct position onto the video image recorded by the image recording device and in addition, also graphical or text identifications signaling a "match" or "no match".

Any movement of the mobile data processing device is in turn detected by the system and results in recalculation of the superimposed information, so that there is again a correct display of the virtual representation in terms of location and perspective in relation to the new position of the mobile data processing device within or above the video image. Such recalculation or correction of the representation is preferably performed live so that the user when viewing the display device always receives easily comprehensibly and complete information respectively correctly complementing the perspective of the video image chosen by him (via the video camera).

A similar functionality, however, can also be obtained with stationarily arranged image recording devices, although this focuses on having the image recorded and stored by the image recording device be superimposed on the live image, preferably next to the other information about the position and/or location, or the "match" or "no match", so that the operator receives an easily comprehendible "manual", how he can again reproduce the recorded situation in the creation of the virtual representation, preferably by coarse arrangement by superposition of the recorded images and by subsequent fine adjustment by re-positioning and storing, until the system outputs a signal for all high-frequency transceivers representing a "match" and possibly releases an interlock.

In a particularly preferred embodiment, the target and/or actual positions and/or locations, and the virtual representation and possibly also the graphical representation of a "match" or "no mach", respectively, each preferably being three-dimensional information (3D- information), in observance of the transformation information and the perspective of the image recording device, which in the case of a mobile data processing device can be determined by means of its position and/or location, are displayed as a projection into a display area of the display device of the at least one data processing device in order to thus provide the viewer of the display device with a representation via the display device being perspectively accurate and spatially correctly displaying the situation. Such a projection of 3D-information in the display area while observing the perspective of the viewer of the display device is known, for example, from ray tracing technology and, in a manner possibly adapted to the situation of application, can be used for the present invention.

Such projection of all 3D-information in the display area with simultaneous superposition of a live image recorded by an image recording device enables the user of the system according to the invention both accurate visual perception and restoration of a recorded situation, which, however, can at the same time by the virtual representation and the definitions established therein of the target positions and/or locations of the high-frequency transceivers, be verified in an automated and highly accurate manner.

In a preferred system according to the invention, RFID-markers are used as high-frequency transceivers, where these markers can transmit and receive preferably in a plurality of frequency bands and, moreover, programming of the markers is possible. In particular, preferably so-called passive RFID-markers are used, i.e. those which do not comprise their own power supply in the form of a long-life battery or the like. Such RFID-markers are preferably supplied with power by the electromagnetic field of the transmission device for activating them and thereafter possibly receiving necessary commands, which then lead to the transmission of a response sequence by the RFID-marker. The response sequence can contain both information stored by the marker, such as the identification and further information stored by earlier programming, or for reading out data recorded by the marker, such as e.g. a measured temperature, radiation dose or the like.

The system according to the invention is used in a variety of applications, in particular in those applications where accurate reproduction of positioning objects and/or humans is required. In particular, a system according the present invention is used, in which controlling the positioning of a plurality of high-frequency transceivers relative to each other and/or absolutely within the virtual representation, where the high-frequency transceivers are arranged in particular on one or more objects and/or on individuals. Particularly preferably, the system according to the invention is used for reestablishing the assembly of high-frequency transceivers after loss of the relative position to each other and/or the absolute position in relation to the virtual representation, in particular for repositioning a human and/or objects relative to a human.

The fields of application of the present invention are numerous and range from aeronautics via vehicle technology to data-processing technology, robotics and medicine. Therefore, in the framework of the following description, only individual cases can be mentioned in detail. Any restrictions of the very general teaching of the present invention as it has been illustrated above and as it additionally arises for the person skilled in the art therefrom, however, are explicitly not intended by the descriptions of individual embodiments.

The features and advantages of the present invention result at least partly also from the following detailed description of various embodiments of the invention in combination with the drawings and the claims.

Figure 1:
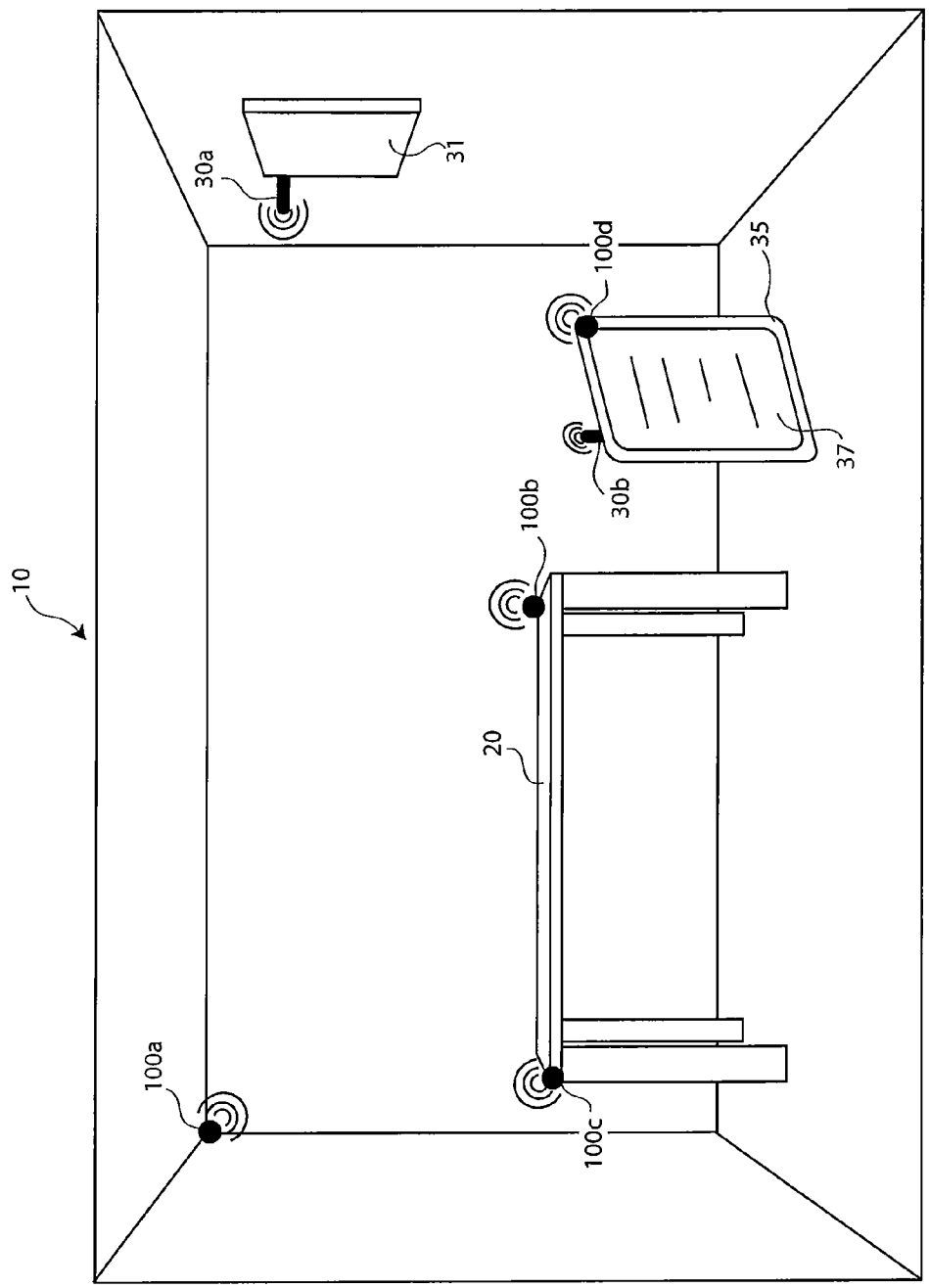
FIG. 1 shows a schematic representation of a first embodiment of the present invention in a first general situation of application.

FIG. 1 shows a schematic representation of a first embodiment of the present invention by way of example in a first general situation of application. In a (real) space 10, an object 20 is arranged, which at two points, in the example of FIG. 1 being located at its opposite corners, is provided with high-frequency transceivers 100b, 100c in the form of RFID-markers. There is also a further stationary RFID-marker 100a arranged in one corner area of the space 10. Preferably, the RFID-markers are of the passive type and, for example, being self-adhesive, whereby easy application of the same is possible. All RFID-markers in the present embodiment comprise an individual identification so that any confusion of markers is not possible.

Furthermore, a combined transmission and reception device 30a is disposed within the space 10 with an associated antenna signal processing device 31. The transmission and reception device 30a is designed such that the antenna can be operated both as a transmitting as well as a receiving antenna, where the respective switching of operation of the antenna signal processing device 31 is at least partially controlled.

A data processing device 35 is connected to the antenna signal processing device 31 via a suitable communications link, such as infrared, WLAN or the like, so that the data processing device 35 can with the antenna signal processing device 31 in particular exchange data, control formation, and position and/or location information as well as identification information. The data processing device 35 comprises a graphical display device 37 with which a user is presented visual information. Preferably, the data processing device 35 is of the mobile kind, for example, a tablet computer.

In the embodiment of FIG. 1, the data processing device 35 is also provided with an RFID-marker 100d and further comprises a second reception device 30b which is connected to the mobile data processing device in a suitable manner such that data can be exchanged with the reception device, in particular position and/or location information as well a identification information. In this embodiment, the antenna signal processing device of the second reception device 30b is implemented by respective software running on the mobile data processing device.

In the illustrated embodiment, the RFID-markers 100a, 100b, 100c are designed in a manner that they upon activation by an electromagnetic field being transmitted from the transmitting device 30a, e.g. in the MHz range, transmit a signal which essentially only reflects their identification and possibly other signal sequences which are beneficial for precise localization and/or determination of the location of the markers 100a, 100b, 100c. Moreover, the markers 100a, 100b, 100c are designed such that the signal emitted by them is both in the MHz-range as well as in the GHz-range, so that quasi two signals are transmitted in different frequency bands. In contrast, the RFID-markers 100d is designed so that its "response signal" is transmitted in only one frequency band, and preferably the one which is not received by the reception device 30 of the mobile data processing device. It is thereby ensured that in the embodiment shown in FIG. 1, after activation of the RFID-markers 100a-100d, the markers 100a, 100b, 100c are "seen" or "heard" by both the reception device 30a as well as the reception device 30b, however, marker 100d only by the reception means 30a. Such a preferred embodiment has some advantages as will be evident from the following description of FIGS. 1 and 2.

Figure 2:
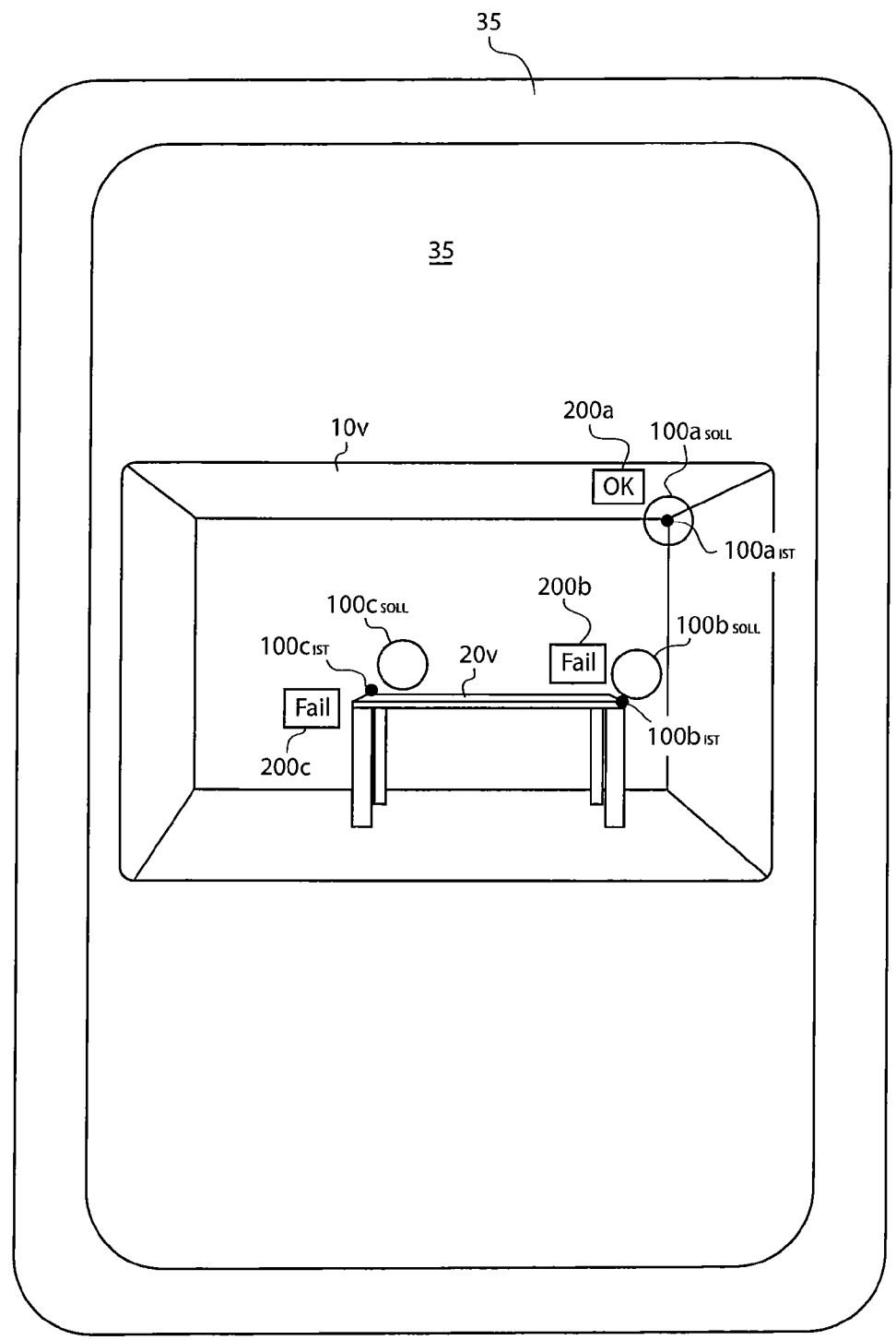
FIG. 2 shows a schematic representation of a display of the display device of the first data processing device according to FIG. 1.

The situation of application and the function of the embodiment of the invention presently shown is described with reference to FIG. 2 and, if necessary, to FIG. 1. FIG. 2 shows the image displayed on the graphical display device 37 of the mobile data processing device 35, at least partially. In this, it can be seen that the representation of the spatial situation has a different perspective than the situation shown in FIG. 1, which is due to the fact that the mobile data processing device 35, as indicated in FIG. 1, "views" the situation of FIG. 1 from the side. In this, the displayed image represents a virtual representation of the situation, where the space 10 corresponds to the real space 10v and the schematized object 20v corresponds to the real object 20.

The perspective selected for the display of FIG. 2 can presently be determined by the system according to this embodiment in two different ways: firstly, by means of the reception device 30a, the transmission signal of the RFID-marker 100d is detected which is attached to the mobile data processing device and on the basis of which the position and/or location of the data processing device is determined in relation to the reception device 30a. This position and/or location information is then transmitted to the data processing device 35 which based on the transformation information accessible to it and determined for this application situation in a calibration process—not described—can determined its position within the virtual representation. Secondly, the mobile data processing device 35 can also itself perform a determination of a position and/or location, namely, in that it detects the transmission signal transmitted by the RFID-markers 100a via the reception device 30b and based on the detected position and/or location information and the transformation information stored in the memory device (which can be disposed within the mobile data processing device) determines its own position and/or location within the virtual space (i.e. the virtual representation).

The position and/or location thus determined of the mobile data processing device 35 is then used as the basis for the calculation of the display, so that it displays the virtual representation of the situation "from the perspective" of the mobile data processing device. This functionality of the present invention is particularly interesting when a portable display device is used as a display means—not shown in the figures—which is designed in the form of a pair of glasses, and by means of which image projection of the display is effected onto the retina of the user. Determining the position and/or location of the glasses and therefore the head position and the viewing direction of the user can again be performed using a high-frequency transceiver and/or a transmission and/or reception device being disposed on the glasses, and thereby projecting a perspectively correct representation of the virtual representation with respect to the user's viewing direction in a kind of 3D-glasses or also VR-glasses (VR Virtual Reality) into the user's field of vision.

It needs no further explanation, that the two possibilities discussed for determining the position and/or location of the mobile data processing device within the virtual representation can also be applied cumulatively, in order to in this manner compensate and/or correct possible errors and/or deviations of the transformation information which are valid for the respective transmission and reception frequencies.

Such deviations of the transformation information of the various transmission and reception frequencies can also be used for detection of objects or individuals in the spaces respectively supplied with the antenna arrays (also with the RFID-markers), because they—in general—for different frequencies of electromagnetic radiation, reflect or absorb differently and thus cause different field distortions and dampening, which can be determined by comparing the transformation information against each other, at least qualitatively, but also possibly quantitatively.

The virtual representation displayed by the display means 37 of the mobile data processing device 35 also shows the actual positions and/or locations $100a_{IST}$-$100c_{IST}$ of the RFID-markers 100a -100c within the virtual representation, shown here as solid dots, determined by the system on the basis of the determination of the position and/or location of the reception systems 30a and 30b and the respective transformation information. In addition, the target positions and/or locations $100a_{SOLL}$-$100c_{SOLL}$ of the respective markers 100a -100c stored within or in relation to the virtual representation in the memory device, are displayed, presently as transparent circles. The actual positions and/or locations $100a_{IST}$-$100c_{IST}$ as well as the target positions and/or locations $100a_{SOLL}$-$100c_{SOLL}$ are like the virtual representation themselves displayed correctly in perspective, i.e. "from the perspective" of the mobile processing device 35.

As can be seen, there is a "match" between the target and the actual position and location of the marker 100a, that is, the detected position and/or location of the marker based on the transformation information has the correct position which within the virtual representation within the framework of the accuracy required with its determination of the target position and/or location could be indicated, for example, by the size of the transparent circle. The "match" is additionally confirmed in a manner quickly and visually easily comprehensible by the user by means of the text display "OK" 200a. The actual position $100b_{IST}$, $100c_{IST}$ of the two markers 100b and 100c, however, does not correspond to their target position $100b_{SOLL}$, $100c_{SOLL}$, so there is "no match", which is also displayed by the text display "FAIL" 200b, 200c.

As a result, the viewer of the display device can in this embodiment therefore directly recognize that the position of the object 20 in relation to its target position, which results from the target positions and/or locations $100b_{SOLL}$, $100c_{SOLL}$, is located incorrectly, and can by means of the representation—in correct perspective—of the display device perform displacement or relocation of the object 20, for so long until a "match" is displayed for the markers 200b and 200c i.e. a respective "OK". In this, any likelihood to confuse, for example, the markers 100b and 100c is excluded due to the individual identifications of the marker 100a-100d, which are, preferably both recorded together with their positions and/or locations as well as, preferably, stored within the virtual representation, so that erroneous placement of the object 20 can be detected by the system and certainly be shown within the virtual representation, even if the position and/or location of the object 20 seems to be correct in real space, for example, due to a symmetry of the object.

Alternatively to the text displays 200a-200c, also color variations of the respective icons can be displayed for each pair consisting of the target positions and/or locations $100a_{SOLL}$, $100b_{SOLL}$, $100c_{SOLL}$ and the actual positions and/or locations $100a_{IST}$, $100b_{IST}$, $100c_{IST}$, so that, for example, the icons for the target and the actual positions and/or locations of the marker 100a have a green color, and the target and the actual positions and/or locations of the marker 100b, 100c, have a red color, where when changing from "no match" to "match", a color change would likewise make sense.

By means of the two-fold possibility of determining the position and/or location described above with reference to the reception systems 30a and 30b based on different transmission and reception frequencies, also in the case of the determination of the position and/or location of the RFID-markers 100a-100c, a similar redundant detection of these positions and/or locations can occur, which again by means of the respective transformation information should lead to congruent actual positions and/or locations of the markers within the virtual representation. Deviations from the congruency can thus on the one hand be compensated or be an indication of the presence or incorrect storage of other objects and/or individuals in the space. Ideally, such objects and/or individuals, however, can themselves be provided with respective markers and unique information can be recorded by the system in this regard.

A video representation of the situation recorded by an image-recording device, such as a video camera, integrated within the mobile data processing device 35, can, for example, be underlaid to the displayed representation of the virtual representation and should ideally essentially match the representation of the virtual representation in perspective. In this manner, further information facilitating detection of the situation can be provided for the user, which can be regarded as a kind of supplement to the "artificial" representation of the virtual representation.

Figure 3:
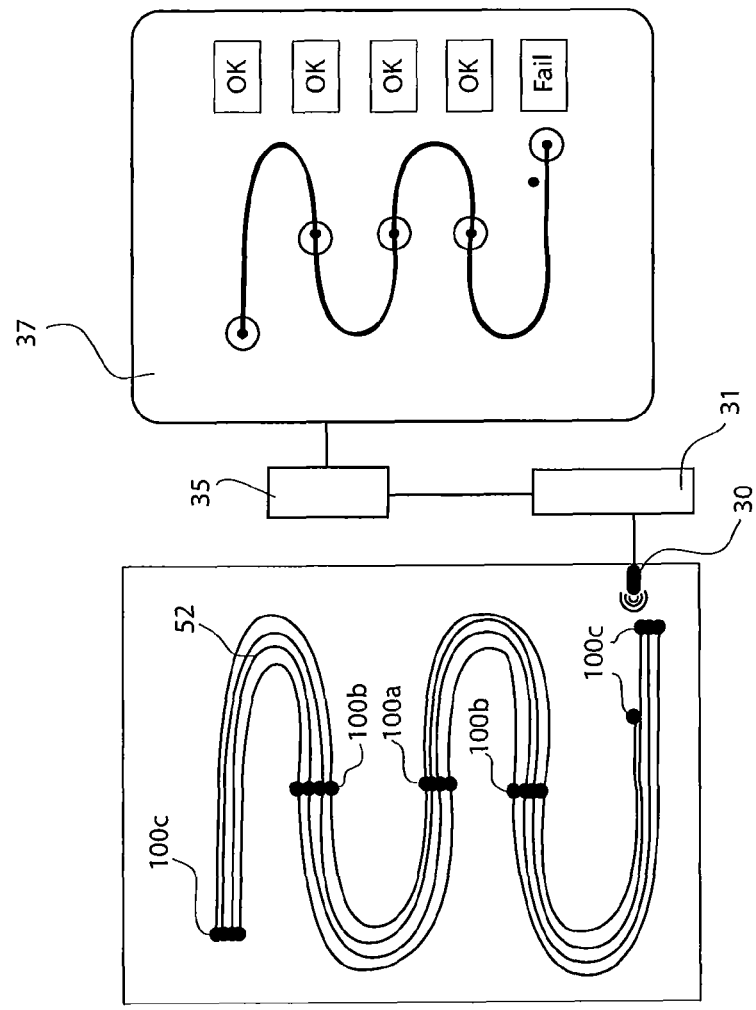
FIG. 3 shows a schematic representation of a further situation of application of a further embodiment of the present invention.
Figure 3:
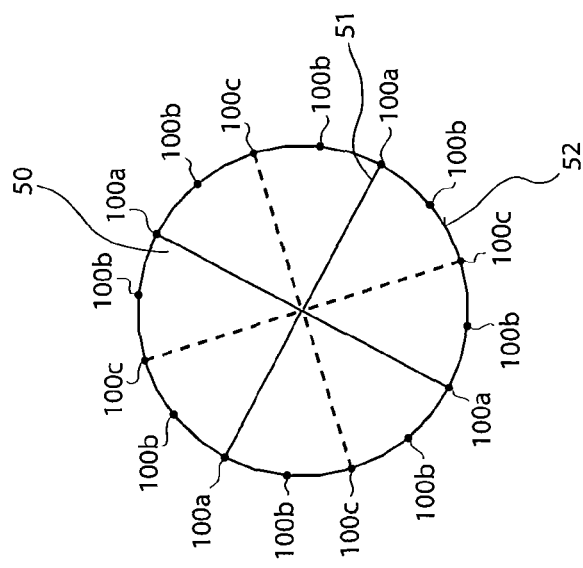

The following FIG. 3 to now show specific situations of application of the present invention, where the respective embodiments of the system according to the invention were adapted accordingly to these situations of application. In order to avoid repetitions and in the interest of a stringent description of these embodiments, reference is also made to the explanations on the description of the function of the system according to the invention according to FIGS. 1 and 2 and to the general description.

FIG. 3 shows the application of the invention in a system—chosen by way of example—for controlling the correct packing of parachutes. For this purpose, as shown in FIG. 3a, first RFID markers 100a are applied to a parachute 50 in the region of the connection of the suspension lines to the canopy or at the intersection of segment seams 51 ad the canopy 50. Third RFID markers 100c are disposed along the canopy edge centered between the first RFID markers 100a and further second RFID markers 100b again centered between each first and third RFID-marker 100a and 100c.

In plan view of the canopy edge 52 then lying in the bundle, first, second and third markers 100a, 100b and 100c then come to lie on top of each other when the canopy is correctly folded, namely, such that all first RFID-markers 100a in the double-S-shaped package come to lie centrally at the same location with the bundle of suspension lines and disposed on top of each other, respective second RFID markers 100b disposed here-above and here-beneath at the canopy edge 52 to the left or to the right, respectively, of each of the first marker 100a come to lie above or below each other, respectively, and third RFID markers 100b respectively disposed between two second markers 100b there-above and therebeneath, respectively, at the canopy edge 52, likewise come to lie above or below each other. This arrangement of the first, second and third markers 100a-100c is also illustrated in FIG. 3b, where FIG. 3b for reasons of clarity does not show the entire parachute package but merely a top view of the canopy edge 52.

The positions and possibly the locations as well as the identifications of all the first, second and third RFID-markers are detected after packing by means of a system according to the invention comprising a transmitting and receiving antenna 30 with an antenna signal processing device 31 connected thereto and a first data processing device 35 with an associated display device 37, and are by means of the transformation information determined by measuring during creation of the system transformed into a virtual representation of the packet comprising the target positions of all corresponding markers along with the information on the required accuracy of the match between the actual and the target positions.

FIG. 3c shows the virtual representation including the actual and target positions of the markers in the present case displayed by the display device 37, as well as additional text information clearly identifying a "match" of the positions. For displaying the actual and target positions within the virtual representation, corresponding icons are used just like in the case of FIG. 2. In FIG. 3b, a third RFID marker 100c did not come to lay in the correct position in the lower part of the package, which is illustrated by a corresponding position of the icon displayed in the lower part of the illustrated virtual representation and due to which, "no match" is displayed for these markers.

In this application, the system according to the invention therefore merely serves to verify the correct arrangement or repositioning of a plurality of RFID-markers, where this repositioning of the marker or markers must also only occur within a range based on the accuracy information stored with the target position.

The embodiment of FIG. 3 can equally be effected without a respective display device 37 and the information displayed therein, but it is sufficient if the data processing 35 outputs a signal indicating a "match" of all markers by means of which, for example, an interlock for delivering the parachute is controlled.

Figure 4:
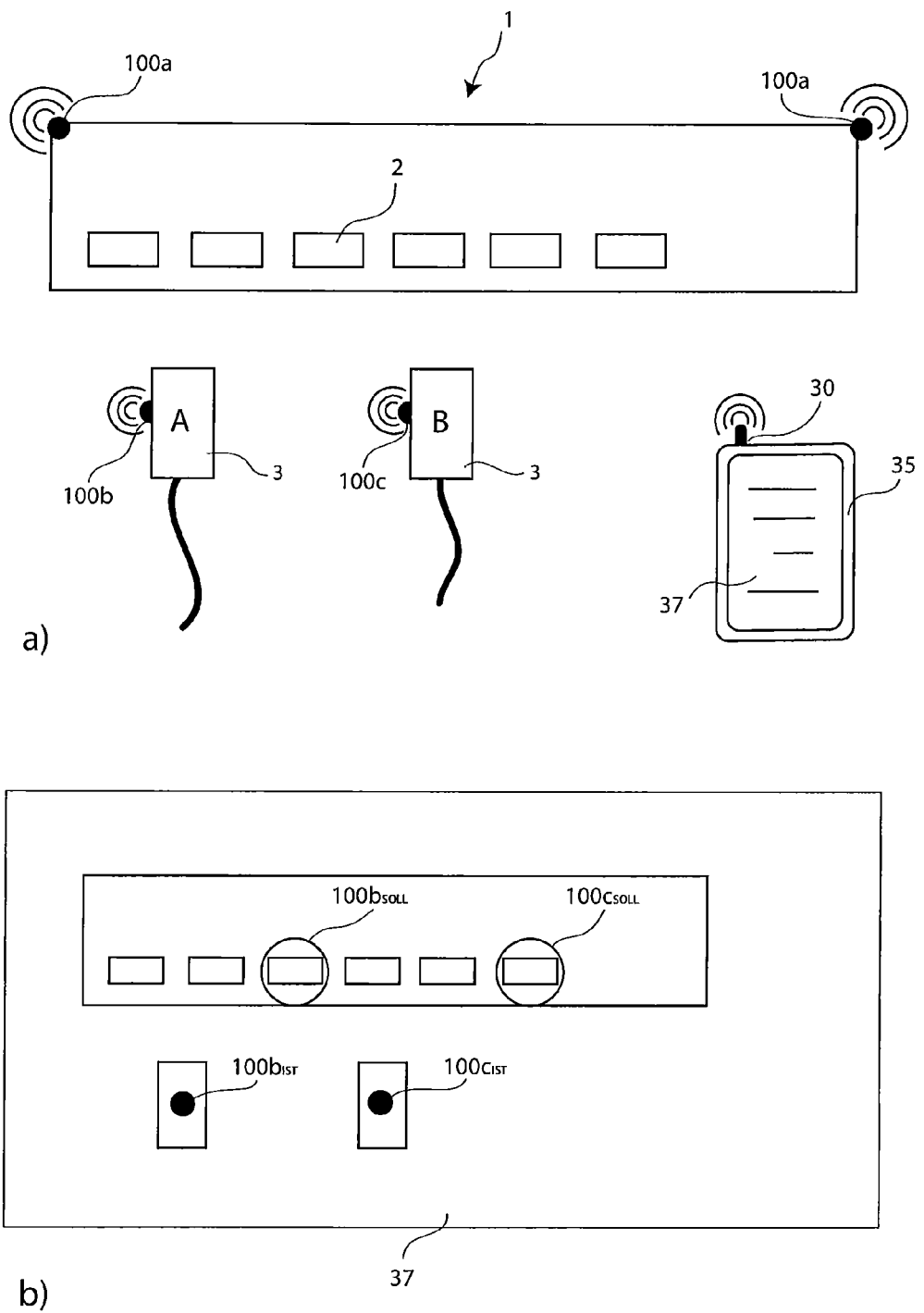
FIG. 4 shows a schematic representation of again another situation of application of a further embodiment of the present invention.

FIG. 4 shows an embodiment or a situation of application, respectively, reaching beyond the simple control function of the embodiment according to FIG. 3 in which there is a user guidance of the system according to the invention. FIG. 4a shows a so-called patch panel 1 of a network or phone distributor having first RFID-markers 100a disposed on being stationary in relation to the patch panel 1.

The patch panel has sockets 2, in which network or telephone connectors 3 are inserted according to a certain predetermined system. Such network or telephone distribution can in large installations be of considerable complexity and when patching or re-patching (i.e. when first connecting connectors into the corresponding sockets or when changing the assignment of a connector to another socket) it is therefore absolutely essential in order to avoid errors, to correctly connect the respective two components with one another, which is guaranteed by the invention.

According to FIG. 4a, the connectors 3 are provided with second and third RFID-markers, where a mobile data processing device 35 with a display device 37 comprises a transmission and reception device 30, with which the signals emitted from the markers are recorded and, for example, due to the phase and amplitude of which, a determination of the marker position is effected. In addition, the identifications transmitted by the markers are recorded and evaluated. The data processing device comprises internal memory in which a virtual representation of the patch panel (or in a simplification, only its surface) is stored.

In this embodiment, the virtual representation does not itself directly comprise the target positions of the second and third (and further) RFID-markers but these positions are stored in a separate database, but with reference to the respective reference system of the virtual representation. In this manner, a simple change of the stored target positions of the RFID-markers is possible, which can be performed locally and thus enables greatest possible flexibility, as this is easily changeable in the decentral database. The data processing device 35, however, also has access to this dataset of target positions of the markers and thus can therefore also assemble a virtual representation for the case of application, which in turn contains the target positions of the markers.

As is shown in FIG. 4b, the mobile data processing device 35 determines its position and location in relation to the patch panel once it is in its vicinity by means of the first markers 100a and based thereupon in a correct perspective displays a virtual representation of the patch panel on the display device and optionally a video image of a video camera being therebehind. Furthermore, the positions of the second and third markers 100b, 100c are determined with respect to the mobile data processing device and transformed into the virtual representation by the transformation information being stored in the data processing device. The virtual representation displays by corresponding icons at least the target position of the second marker $100b_{SOLL}$ and also the actual position of the second marker $100b_{IST}$. Although this is not necessary, it can be useful in complex cases, to display not the target and actual positions and/or locations of all recorded RFID-markers but to proceed in the manner of a display chain, where initially a first marker with its target and actual position is displayed, after confirmation by the user, a second marker with its target and actual position, etc.

In the event that a connector 3 is not plugged into the correct socket 2 (or not at all plugged in), the display of the mobile data processing device will display them (for example, by "FAIL"), and indicate to the user, into which of the sockets 2 of the patch panel 1 the connector 3 needs to be plugged. In this manner, even randomly complex network structures and telephone distribution structures can be altered easily and intuitively, because the user will be guided by the system according to the invention and errors in patching are excluded.

The embodiments described above can with only minor changes or adjustments be transferred to other cases of application. A separate detailed description of such examples is here dispensed with, however, a few such examples shall presently be briefly mentioned and their possible distinctive features outlined:

One application of the system according to the invention in aeronautics is for example the verification of the correct supply of aircrafts with life jackets. For this, all lifejackets have first RFID-markers applied to them, each having an identification associated with the corresponding seat. Additionally, for example, second RFID-markers are disposed in the headrests of the seats characterizing the seating position. A mobile data processing device implemented according to the invention with a transmission and reception system can now upon a movement by the aircraft on the basis of the second markers, being disposed in the headrests and using the transformation information, perform a determination of the position or location and based thereupon display a virtual representation of the aircraft (possibly graphically significantly simplified or distorted) in a perspectively correct manner. A representation of the target positions of the first RFID-markers, however, is not necessary but it is sufficient to clearly indentify the seats of the aircraft within the virtual representation for which the comparison between the actual and target position of the first marker delivers a "no match". Here, the life jackets were either removed or are not in the correct place and must therefore be inspected.

In addition, the RFID-markers attached to the lifejackets can comprise a device with which the age of the respective marker is provided as readable information, whereby after transmission of the age information in association with the identification of the marker to the transmission and or reception system, after its activation, the age of the life jacket is detected and it can optionally be displayed on the display device as being outdated. Finding and replacing outdated lifejackets is in this manner easily possible using the system according to the invention.

In another application of the system according to the invention also in aeronautics, luggage pieces located in the luggage compartment are marked by RFID-markers after completion of the loading process on the basis of the positions of the markers, a virtual representation of the luggage compartment with this initial positions and locations is stored as target positions and/or locations. If during further measurements in the course of the flight, any displacement of the luggage is registered, then this can possibly be adequately responded to, for example by intervention of the cabin crew to the extent possible. Finally, it is also easily possible in this manner, to again retrieve a piece of luggage after being loaded based on the individual identification of the RFID-marker disposed thereon and thereby possibly greatly accelerate unloading of a particular piece of luggage, for example, after a passenger has not shown up, in that there is a search in the luggage compartment within the virtual representation using the system according to the invention and by means of an appropriately equipped mobile data processing device, and the piece of luggage sought can thereby directly be marked.

In another application of the system according to the invention in motor vehicle technology, RFID-markers preferably operating in the GHz-range are disposed in a vehicle passenger compartment at predetermined positions of the belt straps of the safety belts and within the seats. A data processing device according to the invention within the motor vehicle with a transmission and reception system can now by measuring the position of the RFID-markers and based on the transformation information, preferably determined and stored during implementation, determine the correct position of the RFID-markers in the virtual representation and thus on the seat belts, i.e. whether a passenger has correctly put on the seat belt or not. Capturing the occupation of a vehicle seat by a passenger can also be performed thereby, namely, by whether a signal of an RFID-marker mounted in the seat surface at a position displaced by the load can be detected or not. Any displacement by the marker in the virtual representation of the motor vehicle passenger compartment away from the resting position, and thus away from the target position would indicate the presence of a passenger, and this could in the case of the output of a "no match" signal by the data processing device activate the respective airbag in the event of an accident.

In a further application of the system according to the invention in robotics, work pieces to be machined by a robot are equipped with RFID-markers at known points and other additional stationary markers in the area of the robot. On the robot itself, transmission and reception systems according to the invention are mounted which detect the position of all nearby RFID-markers with respect to the receiving system and transform them via the transformation information into a virtual representation of the processing space. If from the perspective of the robot, its position and/or location within the virtual representation is also constantly determined, then any false placement of the work piece marker, i.e. the work piece detected is detected within the virtual representation, and/or a collision with the work piece is in the course of its predetermined path of movement anticipated in the virtual representation, then there is an immediate shutdown of the system to avoid any collision.

In another application in the field of robotics, a robot arm has a plurality of RFID-markers applied at suitable points, which are continuously read out by a transmission and reception system from a point outside the range of movement of the robot and the position and/or location of which is continuously transformed into the virtual representation as actual positions and/or locations. If a deviation between the target and the actual position and/or location is detected within the virtual representation for at least one high-frequency transceiver, then the system determines a displacement vector and on its basis actuates the robot such that the target and actual position and/or location of at least one high-frequency transceiver "matches". Thereafter, the target positions of some or all high-frequency transceivers is replaced with new target and actual positions and/or locations and further displacement of the robot is controlled on the basis of the re-determined displacement vectors. In this manner, complex trajectories can be securely "run" by the system according to the invention with the robot arm.

A further embodiment and situation of application of the present invention will now be described with reference to FIG. 5. This is an application in the field of radiation therapy, in which exact positioning of a patient as well as the coordination of all relevant treatment parameters with the treatment situation is of utmost importance.

Figure 5:
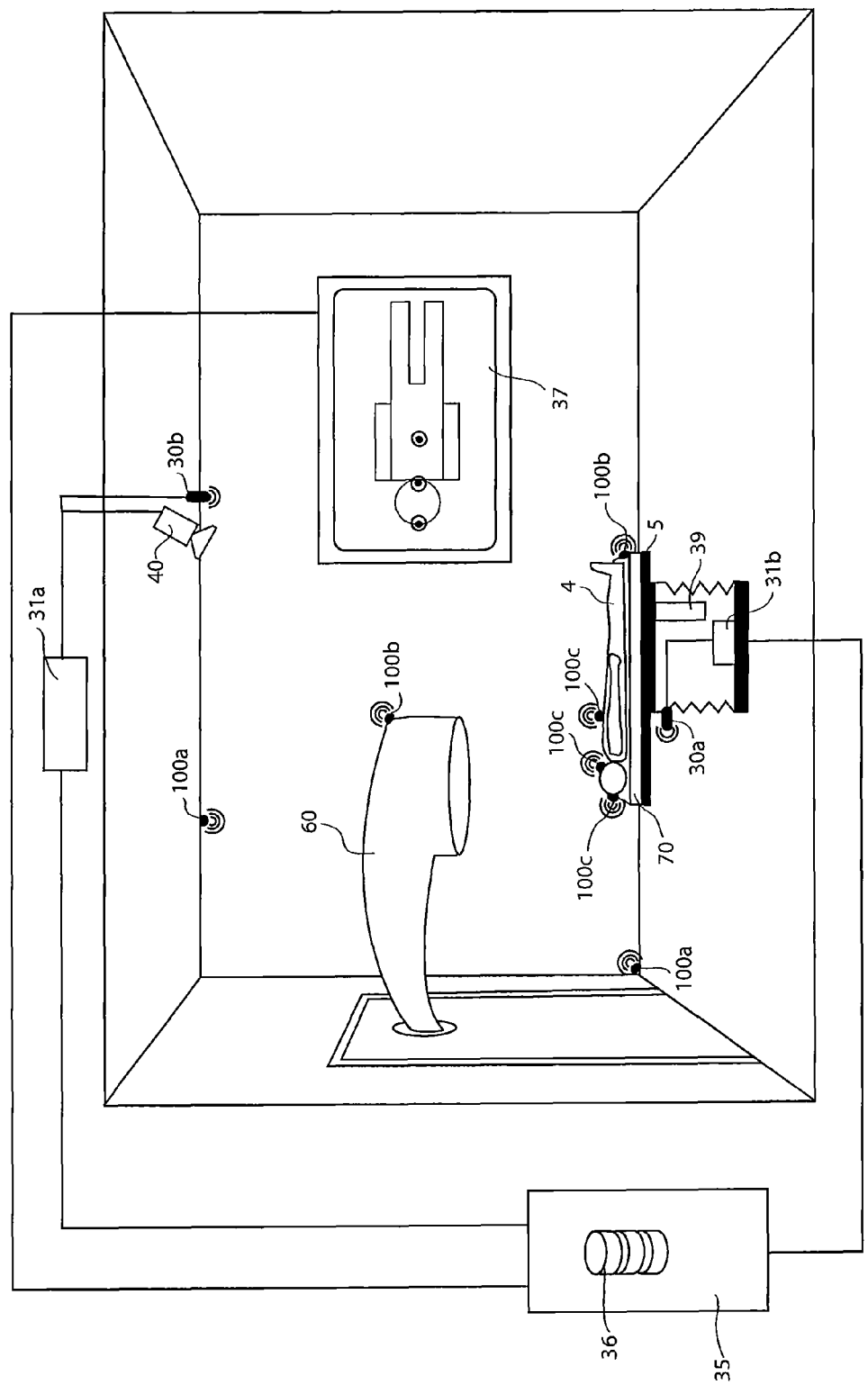
FIG. 5 shows a schematic representation of a further embodiment of the present invention in a further situation of application.

FIG. 5 schematically shows preparation of the patient's treatment in a treatment room for ion beam irradiation. In this, the patient 4 is in a lying manner supported on a treatment table 5 displaceable in all directions of the room and on a patient-specific immobilization means 70 in the form of a vacuum pad, where the isocenter of the radiation is below the gantry 60 and presently within the patient's head. Within the treatment room, first and second transmission and reception devices 30*a*, 30*b* are positioned both directly beneath the treatment table 5, therefore also on the ceiling. The transmission and reception devices 30*a*, 30*b* are connected to corresponding antenna signal processing devices 31*a*, 31*b*, which are in turn connected to a first data processing device 35 preferably arranged outside the room. The data processing device has a memory means 36 comprising a data structure that represents a virtual representation of at least parts of the previously described components of the treatment room and the patient. A video camera 40 as well as a display device 37 are connected with the data processing device 35.

As already described several times and in detail, the transmission and reception systems determine the positions and/or locations of the RFID-markers 100*a*, 100*b*, 100*c* distributed in the treatment room and transform them as actual positions and/or locations into the virtual representation. In this, the stationary RFID-markers 100*a* serve both verification of the determination of the position and/or location, as well as the determination of the compensation factors for possible interference by the gantry 60, the treatment table 5 and its actuators 39, respectively, and/or any possible further objects in the treatment room.

A graphical representation of the virtual representation is shown well visible for the operator on the display device 37, where, as seen in FIG. 5, only the arrangement of some RFID-markers 100*b*, 100*c*, and the patient 4 on the vacuum pad 70 are shown. Further objects used for radiation treatment, however, presently for reasons of clarity and simplicity presently not mentioned, such as a support mat, a breast board and the like, can in the same manner be included in the detection and the display within the virtual representation.

By means of the system according to the invention, the patient 4, having been marked in an initial examination, for example, with RFID-plasters which have a unique identification in easily accessible locations, can be repositioned in exactly the lying position that he was in during the initial examination/implementation or during previous treatment sessions. Within the framework of the initial examination, an individual virtual representation of the treatment situation is created for each patient to which both the positions and/or locations of the RF-ID-markers on the patient as well as those of the vacuum pad 70 and the gantry 60 and the stationary markers are added as target positions and/or location with their respective individual identifications. Furthermore, during the initial examination or implementation, an image of the patient recorded by the video camera 40 is recorded in the correct position and also added to the virtual representation.

By means of the individual identification of the RFID-markers on all treatment spots relevant for the patient, such as the vacuum pad 70, it can be ensured that false treatment or a confusion of treatment components cannot occur. Moreover, the system can already when the patient enters the room detect his identity using the identification of the RFID-markers and based thereupon the proper treatment parameters for the patient, such as the position of the gantry, radiation dose, aperture settings and the like can be set to prevent any confusion.

Hereafter, repositioning of the patient and the treatment components is performed by the operator using the virtual representation displayed by the display device 37 including the target and the actual positions of essential RFID-markers and optionally a superimposition of a live video image over a video image recorded during the set-up. In addition, the system can, based on the displacement vectors which can be determined using the actual and target positions and/or locations, also perform automated repositioning of the patient. Once all target and actual positions of the RFID-markers "match", the system displays this and the treatment can commence.

If the system detects an incorrect repositioning of the patient, because "no match" between the target and the actual position and/or location of at least one RFID-marker was detected, then the system shall not release an interlock for commencement of the treatment. Likewise, the system can detect the presence of operating personnel in the room by detecting an RFID-marker attached thereto, and also in this case not release the interlock for commencement of the treatment. It is equally possible that upon detection of a "no match" between the target and the actual position and/or location of at least one RFID-marker during the treatment, for example, due to movement of the patient, an immediate interruption of the irradiation is effected, and on the basis of one or more displacement vectors which can be continuously determined also during treatment using the actual and target positions, and/or locations, an automated repositioning of the patient is performed before the irradiation is continued.

Ultimately, it is also possible, to continuously determine displacement vectors during the treatment, for example, for the RFID-markers disposed on the patient, and thereby, for example, following a motion of a tumor in the chest area caused by the patient's breathing, to achieve dynamic relocation of the patient's position by means of the actuators 39. This would create a situation in which the isocenter of the radiation is always in the tumor and therefore maximum treatment success with minimal damage to healthy tissue is achieved, even under the difficult conditions of a non-stationary tumor position.

Also in the case of application illustrated, in addition to the display device, a mobile data processing device—not shown—can be used in addition to the data processing device 35. In this, the mobile data processing device receives the virtual representation from the data processing device 35 for displaying, where the mobile data processing device performs a perspectively correct display of the virtual representation on the basis of its own position and/or location within the virtual representation. Alternatively, the position and/or location of the mobile data processing device can also be determined by the system due to an RFID-marker attached thereto and the image of the virtual representation provided to the data processing device 35 for displaying can on this basis be computed in real-time perspectively correct "from the perspective" of the mobile data processing device.

By means of the two transmission and reception systems 30*a*, 30*b*, 31*a*, 31*b*, as previously described, redundant determination of the actual positions of the RFID-markers can occur within the virtual representation, or a first supplementary determination with differing accuracy, for example, due to the use of different transmission and reception frequencies. Moreover, in this manner, the correctness of the transformation information and thereby the measurement accuracy of the system can be continuously monitored and corrected if necessary.

By storing a plurality of data records of target positions and/or locations for the treatment of a patient who, for example, has multiple tumors, entire treatment protocols can by means of the system according to the invention be processed for a patient in a single session on a similar basis as in the option of "running through" predetermined trajectories described in more detail within the framework of the robotics application, so that, for example, in a first treatment step, a first irradiation of a carcinoma is performed in a first position of the patient at a first predetermined angle of inclination of the gantry 60 using a first dose and for a first duration, and thereafter, there can be an interruption of the irradiation and automatic repositioning of the patient to a second position and a rotation of the position of the gantry 60 to a second predetermined angle of inclination, after which a second further treatment of a second carcinoma with a second dose and for a second duration takes place. Other treatments with respective interposed automatic "repositionings" are of course also possible, where each of the treatment sessions can be executed on the basis of a completely unique set of treatment parameters.

The present invention has been described above both generally and thereafter with reference to preferred embodiments and situations of application with their individual characteristics. All of the characteristics described can be combined almost arbitrarily, where there is a possible restriction only by the respective situation of application and the embodiment related thereto. However, it is expressly pointed out that any combination of characteristics, as described above is possible and within the scope of the description of the invention is also to be considered disclosed as explicitly belonging to it.

The invention claimed is:

1. System for detecting the position and/or location of at least one high-frequency transceiver (100), comprising:
   at least one receiving antenna (30) set up such that high-frequency signals transmitted by said at least one high-frequency transceiver (100) can be received;
   at least one transmitting antenna (30) set up for transmitting high-frequency signals of at least one frequency band provided for being received by said at least one high-frequency transceiver (100) and thereby again causing transmission of high-frequency signals by said at least one high-frequency transceiver (100);
   at least one first antenna signal processing device (31) connected to said at least one receiving antenna (30) and which is set up for analyzing said high-frequency signals received by said at least one receiving antenna in order to derive a spatial position and/or location and an identification of said transmitting high-frequency transceiver (100);
   at least one data processing device (35) at least indirectly connected to said first antenna signal processing device (31) and receiving information therefrom about the position, location, and/or identification of said respectively transmitting high-frequency transceiver (100) and having a display device (37);
   characterized in that
   a data structure is provided in a first memory device (36) connected to said at least one data processing device (35) and at least partially comprising a virtual representation of said space supplied by the antenna field of said at least one transmitting antenna, wherein said virtual representation comprises information about the target position and/or location (100SOLL) of at least one high-frequency transceiver (100) having a predefined identification; and
   transformation information is available to said at least one data processing device (35) on the basis of which an actual position and/or location (100IST) of at least one high-frequency transceiver having a predefined identification within the virtual representation is associated on the basis of the position, location, and/or identification information obtained from said first antenna signal processing device (31);
   said at least one data processing device (35) carries out a comparison between said target position and/or location (100SOLL) and said actual position and/or location (100IST) of a high-frequency transceiver (100) of a predefined identification within said virtual representation, outputting a signal representing a "match" or "no match" for further processing as the result of said comparison; and
   there is a projection of 3D-information in said display area of said display device of said at least one data processing device and in particular projection of 3D-information such as e.g., spatial position and/or location from a perspective of a viewer of said display device.

2. System according to claim 1, characterized in that said at least one receiving antenna (30) comprises a matrix of several coacting receiving antennas, where the coaction is controlled preferably by a second antenna signal processing device and/or said first antenna signal processing device (31).

3. System according to claim 1, characterized in that said at least one data processing device (35) is mobile, in particular a portable data processing device and preferably a portable computer (laptop), a tablet computer, a smart device or the like.

4. System according to claim 3, characterized in that said receiving antenna (30) and/or said first and/or second antenna signal processing device (31) is stationarily connected to said mobile data processing device (35), in particular attached thereto.

5. System according to claim 1, characterized in that said first data processing device (35) comprises a plurality of coacting data processing devices, where data communication between said plurality of data processing devices is effected preferably by means of optical, radio or electrical data connections.

6. System according to claim 1, characterized in that said at least one transmitting antenna (30) is said at least one receiving antenna (30).

7. System according to claim 1, characterized in that said at least one receiving antenna (30) and/or said at least one transmitting antenna (30) are set up such that they can receive and transmit, respectively, on a plurality of frequency bands and in particular said at least one receiving antenna (30), said at least one transmitting antenna (30) and/or said first and/or second antenna signal processing device (31) are set up such that transmitting or receiving high-frequency signals is possible at least substantially simultaneously or variably in the frequency domain across a plurality of frequency bands.

8. System according to claim 1, characterized in that said actual position and/or location ($100_{IST}$) of said at least one high-frequency transceiver (100), said target position and/or location ($100_{SOLL}$) of said at least one high-frequency transceiver (100) and/or said virtual representation are graphically output by a display device (37) connected at least indirectly to said data processing device (35).

9. System according to claim 1, characterized in that said virtual representation comprises information on the required accuracy of the position and/or location determination of said at least one high-frequency transceiver (100), and in particular, in connection with said target position and/or location ($100_{SOLL}$) of at least one high-frequency transceiver with respectively predefined identification, the information on the required accuracy of the position and/or location match between said target and actual position and/or location of said high-frequency transceiver (100) is specified.

10. System according to claim 9, characterized in that said data processing device (35), as a result of said comparison of said target to said actual position and/or location of said at least one high-frequency transceiver, outputs a signal representing a "match" or "no match" for further processing, if said actual position and/or location ($100_{IST}$) of at least one high-frequency transceiver matches its target position and/or location ($100_{SOLL}$) in said virtual representation within the scope of the required accuracy specified.

11. System according to claim 1, characterized in that, in the event that said data processing device (35), as a result of said comparison of said target to said actual position and/or location of said at least one high-frequency transceiver (100), outputs a signal for further processing representing "no match", a displacement vector is formed within said virtual representation between said actual position and/or location and said target position and/or location of said at least one high-frequency transceiver (100), and displayed by said display means (37) of said data processing device (35) and/or serves as a basis for controlling at least one actuating element (39) in order to bring said at the least one high-frequency transceiver (100) into its target position and/or location.

12. System according to claim 1, characterized in that said comparison result is at least in part output in the form of a color-coded visual output, such as a green field or a green dot, or a red field or a red dot, respectively, by outputting text result messages (200), such as "OK" or "FAIL", respectively, by outputting speech and/or by releasing or blocking at least one interlock, preferably at least one software interlock when said data processing means (35) outputs a signal representing a "match" or "no match", respectively, as said comparison result.

13. System according to claim 1, characterized in that said at least one data processing device (35) is connected at least indirectly to at least one external image recording device (40) and/or comprises at least one integrated image recording device, where said image recording device (40) preferably comprises a video camera, and especially preferably, a high-resolution video camera.

14. System according to claim 13, characterized in that at least one image recorded by said external and/or integrated image recording device (40) is stored in said memory device (36) together with or in connection to said virtual representation, where said image is preferably prior to being stored subjected to image processing, in particular contrast enhancement, segmentation, edge detection, subtraction and the like.

15. System according to claim 13, characterized in that superimposition of said image and/or text output of said comparison result and/or of said stored image occurs with said image recorded by said image recording device and this superimpositioned image is output by said display device (37) of said at least one data processing device (35).

16. System according to claim 1, characterized in that said position and/or location of said at least one receiving antenna (30), in particular when the latter is stationarily connected to said mobile data processing device (35), is determined based on said transformation information in relation to said virtual representation and/or at least one determined actual position and/or location of at least one high-frequency transceiver (100).

17. System according to claim 1, characterized in that said transformation information is determined and/or calibrated by determining said actual position and/or location of at least one stationary high-frequency transceiver (100) with predefined identification and relating said actual position and/or location to its target position and/or location of said virtual representation.

18. System according to claim 1, characterized in that said transformation information is determined and/or calibrated by measuring the directional characteristics of said at least one receiving antenna (30) and said relating to said virtual representation.

19. System according to claim 1 characterized in that there is also information of said virtual representation according to the ray-tracing technology in said display area of said display device of said at least one data processing device.

20. System according to claim 1, characterized in that said at least one high-frequency transceiver (100) is an RFID-device (Radio Frequency Identification-Device).

* * * * *